United States Patent [19]

Löhr et al.

[11] Patent Number: 5,504,081
[45] Date of Patent: Apr. 2, 1996

[54] COMBATING FISH PARASITES

[75] Inventors: Reinhold Löhr, Bergisch Gladbach; Hans-Christian Mundt, Erkrath; Peter Andrews, Wuppertal, all of Germany

[73] Assignee: Bayer Aktiengesellschaft, Leverkusen, Germany

[21] Appl. No.: 125,434

[22] Filed: Sep. 22, 1993

[30]     Foreign Application Priority Data

Sep. 29, 1992 [DE]   Germany .................. 42 32 561.7

[51] Int. Cl.⁶ .................. A61K 31/54; A61K 31/505; A61K 31/44
[52] U.S. Cl. .................. 514/225; 514/258; 514/341; 514/343; 514/344; 514/347; 514/351; 514/352; 514/355; 514/356
[58] Field of Search .................. 514/225, 258, 514/343, 341, 347, 356, 355, 352, 344, 351

[56]       References Cited

U.S. PATENT DOCUMENTS

| | | | |
|---|---|---|---|
| 4,531,002 | 7/1985 | Harris | 544/54 |
| 4,590,272 | 5/1986 | Shiokawa et al. | 544/335 |
| 4,647,570 | 3/1987 | Shiokawa et al. | 514/341 |
| 4,678,795 | 7/1987 | Shiokawa et al. | 514/341 |
| 4,687,845 | 8/1987 | Hollowood et al. | 544/54 |
| 4,742,060 | 5/1983 | Shiokawa et al. | 514/252 |
| 4,772,620 | 9/1988 | Shiokawa et al. | 514/341 |
| 4,803,277 | 2/1989 | Shiokawa et al. | 514/332 |
| 4,806,553 | 2/1989 | Shiokawa et al. | 514/332 |
| 4,914,113 | 4/1990 | Shiokawa et al. | 514/333 |
| 4,918,086 | 4/1990 | Gsell | 514/341 |
| 4,918,088 | 4/1990 | Gsell | 514/357 |
| 4,948,798 | 8/1990 | Gsell | 514/275 |
| 4,963,572 | 10/1990 | Gsell | 514/357 |
| 4,963,574 | 10/1990 | Bachmann et al. | 514/357 |
| 5,032,589 | 7/1991 | Shiokawa et al. | 514/245 |
| 5,034,404 | 7/1991 | Uneme et al. | 514/365 |
| 5,034,524 | 7/1991 | Shiokawa et al. | 544/124 |
| 5,039,686 | 8/1991 | Davies et al. | 514/341 |
| 5,051,434 | 9/1991 | Shiokawa et al. | 514/357 |
| 5,066,808 | 11/1991 | Shiokawa et al. | 514/231.5 |
| 5,116,164 | 5/1992 | Casagrande | 405/303 |
| 5,175,301 | 12/1992 | Minamida et al. | 546/272 |
| 5,192,778 | 3/1993 | Kodaka et al. | 514/341 |
| 5,256,679 | 10/1993 | Minamida et al. | 525/85 |

FOREIGN PATENT DOCUMENTS

| | | |
|---|---|---|
| 0163855 | 12/1985 | European Pat. Off. . |
| 0235725 | 9/1987 | European Pat. Off. . |
| 0292822 | 11/1988 | European Pat. Off. . |
| 0407343 | 1/1991 | European Pat. Off. . |
| 0428941 | 5/1991 | European Pat. Off. . |
| 0464830 | 1/1992 | European Pat. Off. . |
| 3712307 | 10/1988 | Germany . |
| 9104965 | 4/1991 | WIPO . |
| 9117659 | 11/1991 | WIPO . |

OTHER PUBLICATIONS

CA 116,128673c, 1992.
CA 111, 097258m, 1989.
CA 116, 123312z, 1992.
Biological Abstracts, vol. 95, 1993, 5222.
J 5 2038–012 (Abstract) 1975 (Derwent).
J 4 9102 823 (Abstract) 1961 (Derwent).
CA 114, 242831m, 1989.
CA 890003459 (1974).
CA 109, 170417c 1988.
CA 116, 214354f 1992.
CA 116, 151580d 1992.
CA 111, 007429r 1989.
CA 117, 026561t 1992.
CA 114, 062097t 1991.
Biology, Seventh Edition, Claude A Villee (1977) pp. 305–310.
Handbook of Acute Toxicity of Chemicals to Fish and Aquatic Invertebrates Waynon W. Johnson & Mack T. Finley (1980).
Gunter Schmahl et al., Parasitol. Res., 75:503–511 (1989).

*Primary Examiner*—Raymond Henley, III
*Assistant Examiner*—Kevin E. Weddington
*Attorney, Agent, or Firm*—Sprung Horn Kramer & Woods

[57]         ABSTRACT

The present invention relates to the use of agonists and antagonists of the nicotinergic acetylcholine receptors of insects for combating fish parasites.

7 Claims, No Drawings

COMBATING FISH PARASITES

The present invention relates to combating fish parasites using agents which contain agonists or antagonists of the nicotinergic acetylcholine receptors of insects.

Intensive fish farming suffers substantial economic losses through damage to the fish which is caused by parasites such as fish-parasitising crustaceans such as, for example, the salmon louse or sea louse. Treatments against these parasites using metriphonate or dichlorvos are known. These active substances must be employed in relatively high concentrations and require a long period of treatment.

Other compounds for combating fish parasites are known from EP-OS (European Published Specification) 407 343.

It has now been found that agonists or antagonists of the nicotinergic acetylcholine receptors of insects are outstandingly suitable for use against parasites in fish.

The agonists or antagonists of the nicotinergic acetylcholine receptors of insects which can be used according to the invention are known from the following publications:

European Published Specifications Nos. 464 830, 428 941, 425 978, 386 565, 383 091, 375 907, 364 844, 315 826, 259 738, 254 859, 235 725, 212 600, 192 060, 163 855, 154 178, 136 636, 303 570, 302 833, 306 696, 189 972, 455 000, 135 956, 471 372, 302 389;

German Published Specifications Nos. 3 639 877, 3 712 307;

Japanese Published Specifications Nos. 03 220 176, 02 207 083, 63 307 857, 63 287 764, 03 246 283, 04 9371, 03 279 359, 03 255 072;

U.S. Pat. Nos. 5,034,524, 4,948,798, 4,918,086, 5,039, 686, 5,034,404;

PCT Applications Nos. WO 91/17 659, 91/4965;

French Application No. 2 611 114;

Brazilian Application No. 88 03 621.

Reference is hereby explicitly made to the generic formulae and definitions described in these publications, as well as to the individual compounds described therein.

These compounds are partly summarised by the term nitromethylenes and compounds which are related thereto.

These compounds may preferably be summarised by the general formula I

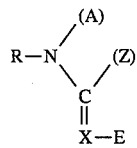

in which

R represents hydrogen, or acyl, alkyl, aryl, aralkyl, heteroayl or heteroarylalkyl, each of which radicals may optionally be substituted;

A represents a monovalent group from the series hydrogen, acyl, alkyl or aryl, or represents a divalent group, which is linked with the radical Z;

E represents an electron-withdrawing radical;

X represents the radicals —CH= or =N—, where the radical —CH= can be linked with the radical Z in place of an H atom;

Z represents a monovalent group from the series alkyl, —O—R, —S—R and

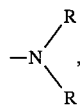

or represents a divalent group which is linked with the radical A or the radical X.

Particularly preferred compounds of the formula I are those in which the radicals have the following meaning:

R represents hydrogen as well as optionally substituted radicals from the series acyl, alkyl, aryl, aralkyl, heteroaryl and heteroarylalkyl.

Acyl radicals which may be mentioned are formyl, alkylcarbonyl, arylcarbonyl, alkylsulphonyl, arylsulphonyl and (alkyl—)-(aryl—)-phosphoryl, which for their part may be substituted.

Alkyl which may be mentioned is $C_{1-10}$-alkyl, in particular $C_{1-4}$-alkyl, specifically methyl, ethyl, i-propyl or sec- or t-butyl, which for their part may be substituted.

Aryl which may be mentioned is phenyl or naphthyl, in particular phenyl.

Aralkyl which may be mentioned is phenylmethyl or phenethyl.

Heteroaryl which may be mentioned is heteroaryl having up to 10 ring atoms and N, O or S, in particular N, as heteroatoms. Thiophenyl, furyl, thiazolyl, imidazolyl, pyridyl or benzothiazolyl may specifically be mentioned.

Heteroarylalkyl which may be mentioned is heteroarylmethyl or heteroarylethyl having up to 6 ring atoms and N, O or S, in particular N, as heteroatoms.

Substituents which may be listed as examples and in preference are;

alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, where the halogen atoms are identical or different and preferably fluorine, chlorine or bromine, in particular fluorine, are the halogen atoms, such as trifluoromethyl, or hydroxyl; halogen, preferably fluorine, chlorine, bromine and iodine, in particular fluorine, chlorine and bromine; cyano; nitro; amino; monoalkylamino and dialkylamino having preferably 1 to 4, in particular 1 or 2 carbon atoms per alkyl group, such as methylamino, methyl-ethyl-amino, n- and i-propylamino and methyl-n-butylamino; carboxyl; carbalkoxy having preferably 2 to 4, in particular 2 or 3, carbon atoms, such as carbomethoxy and carboethoxy; sulpho (—$SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, as well as heteroarylamino and heteroarylalkylamino, such as chloropyridylamino and chloropyridylmethylamino.

A represents hydrogen and represents optionally substituted radicals from the series acyl, alkyl and aryl, which preferably have the meanings given above. Additionally, A represents a divalent group. That which may be mentioned is optionally substituted alkylene having 1–4, in particular 1–2 C atoms, where the substituents which may be mentioned are those listed further above.

A and Z, together with the atoms to which they are bonded, may form a saturated or unsaturated heterocyclic ring. The heterocyclic ring can contain an additional 1 or 2 identical or different heteroatoms and/or hetero-groups. The heteroatoms are preferably oxygen, sulphur or nitrogen, and the hetero-groups N-alkyl, where the alkyl of the N-alkyl group preferably contains 1 to 4, in particular 1 or 2, carbon atoms alkyl which may be mentioned are methyl, ethyl, n- and i-propyl and n-, i- and t-butyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazine.

E represents an electron-withdrawing radical, it being possible to mention in particular $NO_2$, CN or halogenoalkylcarbonyl, such as 1,5-halogeno-$C_{1-4}$-carbonyl, in particular $COCF_3$.

X represents —CH= or —N=

Z represents optionally substituted radicals alkyl, —OR, —SR or —NRR, with R and the substituents preferably having the abovementioned meaning.

Z can, together with the atom to which it is bound and the radical

in place of X, form a saturated or unsaturated heterocyclic ring. The heterocyclic ring can contain an additional 1 or 2 identical or different heteroatoms and/or hetero-groups. The heteroatoms are preferably oxygen, sulphur or nitrogen, and the hetero-groups N-alkyl, with the alkyl or N-alkyl group preferably containing 1 to 4, in particular 1 or 2, carbon atoms. Alkyl radicals which may be mentioned are methyl, ethyl, n- and i-propyl and n-, i- and t-butyl. The heterocyclic ring contains 5 to 7, preferably 5 or 6, ring members Examples of the heterocyclic ring which may be mentioned are pyrrolidine, piperidine, piperazine, hexamethyleneimine, morpholine and N-methylpiperazine.

Compounds which are very particularly preferred for possible use according to the invention, and which may be mentioned, are compounds of the general formulae II and III:

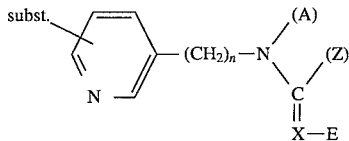

in which n represents 1 or 2, subst. represents one or substituents listed above particularly halogen, in particular chlorine, A, Z, X and E have the abovementioned meanings,

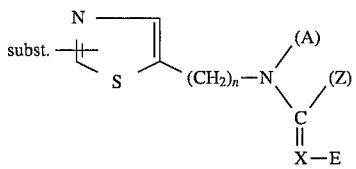

in which the radicals have the abovementioned meaning.

The following compounds may be specifically mentioned:

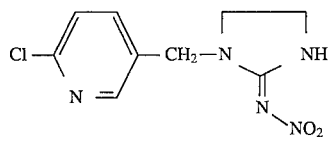

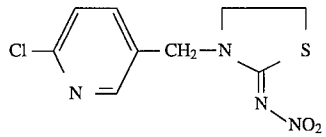

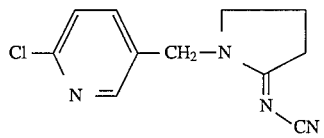

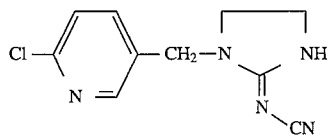

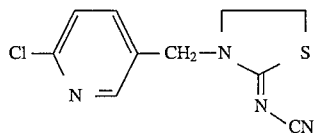

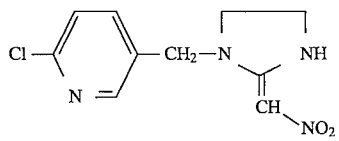

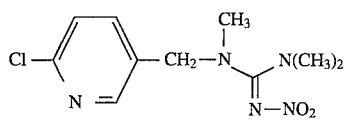

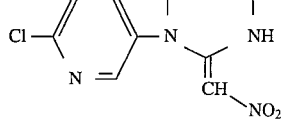

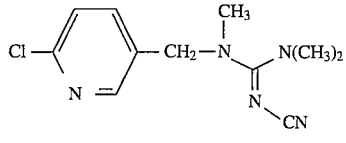

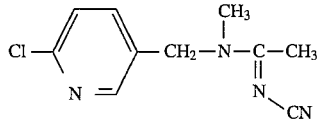

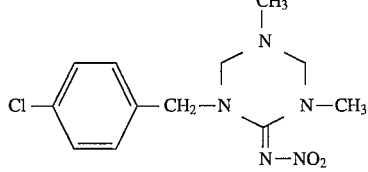

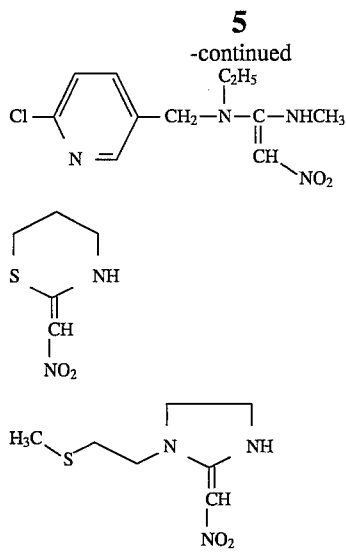

As already mentioned, the compounds which can be used according to the invention may be employed with outstanding effect for combating fish parasites, and in particular fish-parasitising crustaceans. Among these are the Copepodae (cyclops; fish-lice) with the genera
Ergasilus
Bromolochus
Chondracaushus
Caligus (→*Caligus curtus*)
Lepeophtheirus (→*L. salmonis*)
Elythrophora
Dichelestinum
Lamproglenz
Hatschekia
Legosphilus
Symphodus
Ceudrolasus
Pseudocycmus
Lernaea
Lernaeocera
Pennella
Achthares
Basanistes
Salmincola
Brachiella
Epibrachiella
Pseudotracheliastes
and the families
Ergasilidae
Bromolochidae
Chondracanthidae
Calijidae
Dichelestiidae
Philichthyidae
Pseudocycnidae
Lernaeidae
Lernaepodidae
Sphyriidae
Cecropidae
as well as the Branchiuriae (carp lice) with the families Argulidae and the genera Argulus spec.;
as well as the Cirripediae (cirripedes; barnacles) and *Ceratothoa gaudichaudii*.

The fish include food fish, cultivated fish, aquarium fish and ornamental fish of all ages which live in fresh water, sea water and pond water. The food fish and cultivated fish include, for example, carp, eel, trout, whitefish, salmon, bream, roach, rudd, chub, sole, plaice, halibut, Japanese yellowtail (*Seriola quinqueradiata*), Japanese eel (*Anguilla japonica*), red sea bream (*Pagurus major*), sea bass (*Dicentrarchus labrax*), grey mullet (*Mugilus cephalus*), pompano, giltbread sea bream (*Sparus auratus*), Tilapia spp., chichlid species, such as, for example, plagioscion, channel catfish. The agents according to the invention are particularly suitable for treating fish fry, for example carp of body length 2–4 cm. The agents are also very suitable for eel fattening.

The treatment of the fish is effected either orally, for example via the feed, or by balneotherapy, for example a "medical bath" into which the fish are placed and in which they are kept for a period (minutes to several hours), for example in association with being moved from one rearing pool to another. In particular cases, the treatment can also be effected parenterally, for example by injection.

Transient or permanent treatment may also take place of the habitat of the fish, for example in net cages, entire pond installations, aquaria, tanks or pools, in which the fish are kept.

The active substance is administered in preparations which are suited to the uses.

Preparations for oral use are powders, granules, solutions, emulsion concentrates or suspension concentrates which are mixed homogeneously with the feed as feed additives.

Preparations for use as a bath or for treating the habitat are powders, granules, solutions, emulsion concentrates or suspension concentrates, emulsions or suspensions, tablets or the active substance itself. The formulations can be employed by the user in diluted or undiluted form.

The preparations are prepared in a manner known per se, by mixing, granulating, grinding and/or compacting the active substance with solid or liquid carrier substances, optionally with the addition of further auxiliary substances such as emulsifying or dispersing agents, solubilisers, colorants, antioxidants or preservatives.

In contrast to the usual organophosphorus compounds, nitromethylenes are generally sufficiently soluble in water for the concentration to be used, and can therefore also be employed undiluted.

However, more manageable preparations are those in which the active substance is present in diluted form. Suitable diluents for fish and other marine animals and plants are non-toxic substances, which can be liquid or solid, and, immediately prior to use according to the invention, water as well.

For practical use, films are also suitable which contain the active substance in a matrix which is readily soluble in water, or films containing the active, which will be released by diffusion.

The active substance itself, its micronised form or its solid formulations, can be used in water-soluble wrappings, for example in polyvinyl alcohol bags together with the sealed pack. The user is then no longer exposed to the active substance or its formulations.

Semi-solid application forms can also be used for the balneotherapy. The active substance is washed out of greasy or fatty matrices in which it is suspended or dissolved. It is possible to control the release by the choice of auxiliary substances, and of the concentration and form (surface) of the active substance compressions or fusions of hard fats in which the active substance is present are also suitable, in occasion for oral use.

The diluted agents according to the invention are prepared by bringing the active substance of the formula I into contact with liquid and/or solid auxiliary formulation substances by step-wise mixing and/or grinding in such a way that the anti-parasitic activity of the formulation is optimally displayed in conformity with the application.

The formulation steps may be supplemented by kneading, granulating, (granules) and optionally compressing, extruding or moulding (pellets and tablets).

Solid carrier substances, solvents and optionally surface-active substances (surfactants) which are not toxic for the marine flora and fauna serve, for example, as auxiliary formulation substances.

The following auxiliary formulation substances are used for preparing the agents according to the invention:

Solid carrier substances such as, for example, kaolin, talc, bentonite, sodium chloride, calcium phosphate, carbohydrates, cellulose powder, cotton seed meal or polyethylene glycol ether, optionally binding agents such as, for example, gelatin or soluble cellulose derivatives, if required with the addition of surface-active substances such as ionic or non-ionic dispersing agents; in addition ground natural rocks such as calcite, montmorillonite or attapulgite. To improve the physical properties, highly disperse silicic acid or highly disperse absorbent polymers may also be added. Suitable granulated, adsorptive granule carriers are porous types, such as, for example, pumice, crushed brick, sepiolite or bentonite, and suitable non-sorptive carrier materials are, for example, calcite or sand. Beyond this, a multiplicity of pre-granulated materials of inorganic or organic nature, such as, in particular, dolomite or comminuted herbaceous material, can be used. Sorptive organic materials, for example polyacrylates, can also be mixed with the active substance and brought into use.

Suitable solvents are: aromatic hydrocarbons, preferably the fractions $C_8$–$C_{12}$, for example, xylene mixtures or substituted naphthalenes, phthalates such as dibutyl phthalate or dioctyl phthalate; aliphatic hydrocarbons such as, for example, cyclohexane or paraffins, alcohols and glycols as well as their ethers and esters, such as, for example, ethanol, ethylene glycol, ethylene glycol monomethyl ether or ethyl ether, ketones such as, for example cyclohexanone, strongly polar solvents, such as, for example, N-methyl-2-pyrrolidone, dimethyl sulphoxide or dimethylformamide, as well as optionally epoxidised vegetable oils, such as, for example, epoxidised coconut oil or soyabean oil and water.

In each case depending on the nature of the active substance of the formula I to be formulated, suitable surface-active compounds are non-ionic, cationic and/or anionic surfactants having good emulsifying, dispersing and wetting properties. Surfactants are also understood to mean surfactant mixtures.

Suitable anionic surfactants may be so-called water-soluble soaps, as well as water-soluble synthetic surface-active compounds.

Suitable soaps which may be are the alkali metal salts, alkaline earth metal salts or optionally substituted ammonium salts of higher fatty acids ($C_{10}$–$C_{22}$), such as, for example, the Na or K salts of oleic acid or stearic acid, or of natural fatty acid mixtures, which may be obtained, for example, from coconut oil or tallow oil.

Frequently, so-called synthetic surfactants are used, in particular fatty sulphonates, fatty sulphates, sulphonated benzimidazole derivatives or alkylsulphonates.

The fatty sulphonates or fatty sulphates are as a rule present as alkali metal salts, alkaline earth metal salts or optionally substituted ammonium salts and possess an alkyl radical having 8 to 22 C atoms, with alkyl also including the alkyl moiety of acyl radicals, for example the Na or Ca salt of lignosulphonic acid, of dodecyl sulphate or of a fatty alcohol sulphate mixture prepared from natural fatty acids.

Among these are the salts of the sulphuric acid esters and sulphonic acids of fatty alcohol-ethylene oxide adducts. The sulphonated benzimidazole derivatives preferably contain 2 sulphonic acid groups and a fatty acid radical having 8–22 C atoms. Alkylarylsulphonates are, for example, the Na, Ca or triethanolamine salts of dodecylbenzenesulphonic acid, of dibutylnaphthalenesulphonic acid or of a naphthalenesulphonic acid-formaldehyde condensation product.

Additionally, corresponding phosphates, such as, for example, salts of the phosphoric acid ester of a p-nonylphenol-(4-14)-ethylene oxide adduct or phospholipids may be used as auxiliary formulation substances.

Suitable non-ionic surfactants are, in the first instance, polyglycol ether derivatives of aliphatic or cycloaliphatic alcohols, saturated or unsaturated fatty acids and alkylphenols, which may contain 3 to 30 glycol ether groups and 8 to 20 carbon atoms in the (aliphatic) hydrocarbon radical and 6 to 18 carbon atoms in the alkyl radical of the alkylphenols.

Further suitable non-ionic surfactants are the water-soluble polyethyleneoxy adducts, containing 20 to 250 ethylene glycol ether groups and 10 to 100 propylene glycol ether groups, onto polypropylene glycol, ethylenediaminopolypropylene glycol and alkylpolypropylene glycol having 1 to 10 carbon atoms in the alkyl chain. The said compounds usually contain 1 to 5 ethylene glycol units per propylene glycol unit.

Examples of non-ionic surfactants which may be mentioned are nonylphenol-polyethoxyethanols, castor oil polyglycol ethers, polypropylene-polyethyleneoxyadducts, tributylphenoxypolyethoxyethanol, polyethylene glycol and octylphenoxypolyethoxyethanol.

In addition, fatty acid esters of polyoxyethylene sorbitan, such as polyoxyethylene sorbitan trioleate, are also suitable.

The cationic surfactants are quaternary ammonium salts which contain as N-substituents at least one alkyl radical having 8 to 22 C atoms, and possess as further substituents lower, optionally halogenated, alkyl radicals, benzyl radicals or lower hydroxyalkyl radicals. The salts are preferably present as halides, methyl sulphates or ethyl sulphates, for example stearyltrimethylammonium chloride or benzyldi (2-chloroethyl) ethylammonium bromide.

The surfactants which are customarily employed in formulation technology are described, inter alia, in the following publications:

Mc Cutcheon's, Emulsifiers and Detergents, International Edition, New Jersey, USA, 1990;

Suitable binding agents for water-soluble granules or tablets are chemically modified polymeric natural substances which are soluble in water or alcohol, such as starch derivatives, cellulose derivatives or protein derivatives (e.g. methyl cellulose, carboxymethyl cellulose, ethylhydroxyethyl cellulose or proteins, such as zein, gelatin, and the like) as well as synthetic polymers, such as, for example, polyvinyl alcohol or polyvinylpyrrolidone etc. In addition, fillers, (e.g. starch, microcrystalline cellulose, sugar or lactose etc.), lubricants and disintegrants are contained in tablets.

The balneary administration of the agents according to the invention onto the parasites which are to be controlled can be carried out by the agents being added to the cage in the form of solutions, emulsions, suspensions, powders or tablets, where they are rapidly dissolved and dispersed by the movement of the fish and by the water which is flowing through. Concentrated solutions may also be diluted with relatively large volumes of water before being added to the cages. Concentration problems in the cages do not occur, inter alia because the fish at each opening of the cages, become wildly agitated in the expectation of food and thus ensure rapid dilution.

The anti-parasitic agents according to the invention contain, as a rule, 0.1 to 99% by weight, in particular 0.1 to 95% by weight, of active substance of the formula I, and 99.9 to 1% by weight, in particular 99.9 to 5% by weight, of a solid or liquid additive, including 0 to 25% by weight, in particular 0.1 to 25% by weight, of a surfactant.

Whereas concentrated agents are more likely to be preferred as a commercial product, the consumer as a rule uses diluted agents, which he obtains by diluting the commercial product with water.

Such agents may contain yet more additives, such as stabilisers, antifoam agents, viscosity regulators, binding agents, adhesives and other active substances for achieving special effects.

The concentration of the active substance during use depends on the nature and length of the treatment, as well as the age and condition of the fish which are being treated. In the case of a brief treatment, it is, for example, 0.1–100 mg of active substance per litre of water, preferably 0.5–10 mg per litre, in the case of a treatment period of 0.3–4 hours.

In the treatment of ponds, 0.01–50 mg of active substance may be used per litre of water.

Preparations for use as a feed additive are composed as follows, for example:

| a) | Active substance of the formula I | 1–10 parts by weight |
| | Soyabean protein | 49–90 parts by weight |
| | Ground lime powder | 0–50 parts by weight |
| b) | Active substance of the formula I | 0.5–10 parts by weight |
| | Benzyl alcohol | 0.08–1.4 parts by weight |
| | Hydroxypropyl methyl cellulose | 0–3.5 parts by weight |
| | Water | Remainder to 100 |

Preparations for use as a balneotherapeutic are dissolutions, emulsion- or suspension concentrates, for example:

| c) | Active substance of the formula I | 5.0% |
| | Anionic emulsifier | 10.0% |
| | N-Methylpyrrolidone | 25.0% |
| | Mineral oil | 60.0% |
| d) | Active substance of the formula I | 25.0% |
| | Anionic emulsifier | 8.0% |
| | Non-ionic emulsifier | 2.0% |
| | Dimethyl sulphoxide | 35.0% |
| | N-Methylpyrrolidone | 30.0% |
| e) | Active substance of the formula I | 30.0% |
| | Urea | 10.0% |
| | Polyvinyl alcohol | 0.5% |
| | Gum (e.g. xanthan gum) | 0.4% |
| | Preservative | 0.1% |
| | Water | 49.0% |

EXAMPLE A

In-vitro test against salmon louse

Glass dishes are filled with 40 ml of sea water and sufficient 0.1% (weight) or 10% (weight) solution of the active substance in ethanol is added to obtain the desired concentration for use. Sea water without active substance, and sea water which has been mixed with the corresponding quantity of ethanol without active substance, serve as controls.

5 adult salmon lice, which have been removed from naturally infected salmon, are placed in each glass dish. The glass dishes are kept at 10°–12° C. and checked after 1, 2, 5 and 24 hours. A record is taken of the number of test animals which are alive and the number which are dead. The results are summarised in the table:

Active substance:

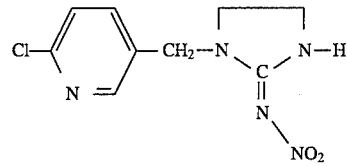

| | Condition of the salmon lice after | | | |
| --- | --- | --- | --- | --- |
| | 1 | 2 | 5 | 24 hours |
| Sea water | 5 alive | | | 5 alive |
| Sea water + 0.04 ml of ethanol | 5 alive | | | 5 alive |
| 1 ppm of active substance | 4 alive 1 dead | 5 dead | | |
| 100 ppm of active substance | 5 dead | | | |

We claim:

1. A method for combatting fish parasites selected from the group consisting of fish parasiting crustaceans from copepodae (fish-lice), branchiurine (carp-lice), cirripedine and cerathothoa gaudichaudii comprising administering to fish having such parasites, or to a habitat of fish having such parasites an effective amount therefor of an agonist or antagonist of the nicotinergic acetylcholine receptors of insects, said agonist or antagonist being selected from the group consisting of compounds of the formula (I):

in which

R represents hydrogen; or represents acyl, alkyl, aryl, aralkyl, heteroaryl or heteroarylalkyl, each of which is optionally substituted;

A represents hydrogen, acyl, alkyl or aryl; or together with Z and the atoms to which they are bonded form a heterocyclic ring;

E represents an electron-withdrawing radical;

X represents —CH= or =N—; or together with Z and the atoms to which they are bonded form a heterocyclic ring;

Z represents alkyl, —O—R, —S—R and —NRR; or together with A or X and the atoms to which they are bonded form a heterocyclic ring;

wherein said "acyl" groups are selected from the group consisting of formyl, alkylcarbonyl, arylcarbonyl, alkylsulphonyl, arylsulphonyl and (alkyl-)-(aryl-)-phosphoryl, which are optionally substituted;

said "alkyl" groups are selected from the group consisting of $C_{1-10}$-alkyl;

said "aryl" groups are selected from the group consisting of phenyl and naphthyl;

said "aralkyl" groups are selected from the group consisting of phenylmethyl and phenylethyl;

said "heteroaryl" groups are selected from the group consisting of thiophenyl, furyl, thiazolyl, imidazolyl, pyridyl and benzothiazolyl;

said "heteroarylalkyl" groups are selected from the group consisting of thiophenylmethyl, furylmethyl, thiazolylmethyl, imidazolylmethyl, pyridylmethyl, benzothiazolylmethyl, thiophenylethyl, furylethyl, thiazolylethyl, imidazolylethyl, pyridylethyl and benzothiazolylethyl;

said "electron-withdrawing radical" is selected from the group consisting of nitro, cyano or halogenoalkylcarbonyl having 2 to 5 carbon atoms and 1 to 5 identical or different halogen atoms; and said "heterocyclic ring" is selected from the group consisting of saturated or unsaturated heterocyclic rings containing 5 to 7 ring members and, in the case of A and Z together, 1 or 2 identical or different heteroatoms and/or hetero-groups in addition to the N depicted in formula (I) and, in the case of Z and X together, 1 or 2 identical or different heteroatoms and/or hetero-groups, the heteroatoms being selected from the group consisting of oxygen, sulphur and nitrogen and the hetero-groups being selected from the group consisting of N-alkyl having 1 to 4 carbon atoms;

and wherein optional substituents are in each case selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, hydroxyl, halogen, cyano, nitro, amino, monoalkylamino and dialkylamino having 1 to 4 carbon atoms per alkyl group, carboxyl, carbalkoxy having 2 to 4 carbon atoms, sulpho, alkylsulphonyl having 1 to 4 carbon atoms, and arylsulphonyl having 6 or 10 aryl carbon atoms.

2. The method according to claim 1, wherein said fish parasites are from the genera Caligus, Lepeophtheirus or Argulus.

3. The method according to claim 1, wherein said fish are from the genera Salmoinidae, Oncorhynchus or Salvelinus.

4. The method according to claim 1, wherein said agonist or antagonist is selected from the group consisting of compounds of the formula (II):

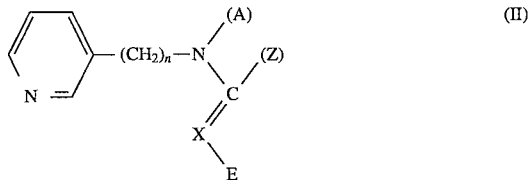

wherein n represents 1 or 2; and the pyridyl ring is optionally substituted by halogen; and A represents hydrogen, acyl, alkyl or aryl; or together with Z and the atoms to which they are bonded form a heterocyclic ring;

E represents an electron-withdrawing radical;

X represents —CH= or =N—; or together with Z and the atoms to which they are bonded form a heterocyclic ring;

Z represents alkyl, —O—R, —S—R and —NRR; or together with A or X and the atoms to which they are bonded form a heterocyclic ring;

wherein said "acyl" groups are selected from the group consisting of formyl, alkylcarbonyl, arylcarbonyl, alkylsulphonyl, arylsulphonyl and (alkyl-)-(aryl-)-phosphoryl, which are optionally substituted;

said "alkyl" groups are selected ,from the group consisting of $C_{1-10}$-alkyl;

said "aryl" groups are selected from the group consisting of phenyl and naphthyl;

said "electron-withdrawing radical" is selected from the group consisting of nitro, cyano or halogenoalkylcarbonyl having 2 to 5 carbon atoms and 1 to 5 identical or different halogen atoms; and said "heterocyclic ring" is selected from the group consisting of saturated or unsaturated heterocyclic rings containing 5 to 7 ring members and, in the case of A and Z together, 1 or 2 identical or different heteroatoms and/or hetero-groups in addition to the N depicted in formula (I) and, in the case of Z and X together, 1 or 2 identical or different heteroatoms and/or hetero-groups, the heteroatoms being selected from the group consisting of oxygen, sulphur and nitrogen and the hetero-groups being selected from the group consisting of N-alkyl having 1 to 4 carbon atoms;

and wherein optional substituents are in each case selected from the group alkylthio having 1 to 4 carbon atoms, halogenoalkyl having 1 to 4 carbon atoms and consisting of alkyl having 1 to 4 carbon atoms, alkoxy having 1 to 4 carbon atoms, 1 to 5 identical or different halogen atoms, hydroxyl, halogen, cyano, nitro, amino, monoalkylamino and dialkylamino having 1 to 4 carbon atoms per alkyl group, carboxyl, carbalkoxy having 2 to 4 carbon atoms, sulpho, alkylsulphonyl having 1 to 4 carbon atoms and arylsulphonyl having 6 or 10 aryl carbon atoms.

5. The method according to claim 4, wherein n represents 1 and the pyridyl ring is substituted by chlorine.

6. The method according to claim 1, wherein said agonist or antagonist is selected; from the group consisting of compounds of the formula (III):

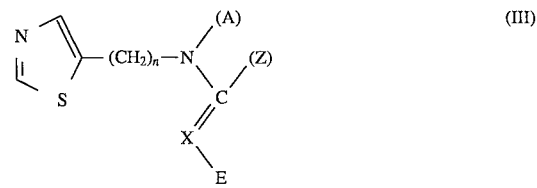

wherein n represents 1 or 2; and the thiazolyl ring is optionally substituted by halogen; and A represents hydrogen, acyl, alkyl or aryl; or together with Z and the atoms to which they are bonded form a heterocyclic ring;

E represents an electron-withdrawing radical;

X represents —CH= or =N—; or together with Z and the atoms to which they are bonded form a heterocyclic ring;

Z represents alkyl, —O—R, —S—R and —NRR; or together with A or X and the atoms to which they are bonded form a heterocyclic ring;

wherein said "acyl" groups are selected from the group consisting of formyl, alkylcarbonyl, arylcarbonyl, alkylsulphonyl, arylsulphonyl and (alkyl-)-(aryl-)-phosphoryl, which are optionally substituted;

said "alkyl" groups are selected from the group consisting of $C_{1-10}$-alkyl;

said "aryl" groups are selected from the group consisting of phenyl and naphthyl;

said "electron-withdrawing radical" is selected from the group consisting of nitro, cyano or halogenoalkylcarbonyl having 2 to 5 carbon atoms and 1 to 5 identical or different halogen atoms; and said "heterocyclic ring" is selected from the group consisting of saturated or unsaturated heterocyclic rings containing 5 to 7 ring members and, in the case of A and Z together, 1 or 2 identical or different heteroatoms and/or hetero-groups in addition to the N depicted in formula (I) and, in the case of Z and X together, 1 or 2 identical or different heteroatoms and/or hetero-groups, the heteroatoms being selected from the group consisting of oxygen, sulphur and nitrogen and the hetero-groups being selected from the group consisting of N-alkyl having 1 to 4 carbon atoms;

and wherein optional substituents are in each case selected from the group consisting of alkyl having 1 to 4 carbon atoms, alkoxy having 1 to 4 carbon atoms, alkylthio having 1 to 4 carbon atoms, halogenoalkyl having 1 to 4 carbon atoms and 1 to 5 identical or different halogen atoms, hydroxyl, halogen, cyano, nitro, amino, monoalkylamino and dialkylamino having 1 to 4 carbon atoms per alkyl group, carboxyl, carbalkoxy having 2 to 4 carbon atoms, sulpho, alkylsulphonyl having 1 to 4 carbon atoms, and arylsulphonyl having 6 or 10 aryl carbon atoms.

7. The method according to claim 5, wherein the compound of the formula (II) is imidacloprid of the formula:

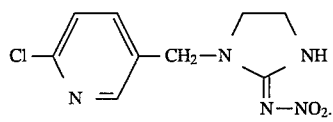

* * * * *

UNITED STATES PATENT AND TRADEMARK OFFICE
CERTIFICATE OF CORRECTION

PATENT NO. : 5,504,081
DATED : April 2, 1996
INVENTOR(S) : Lohr, et al.

It is certified that error appears in the above-indentified patent and that said Letters Patent is hereby corrected as shown below:

Col. 12, lines 27-30    Delete " alkylthio having 1 to 4 carbon atoms, halogenoalkyl having 1 to 4 carbon atoms and consisting of alkyl having 1 to 4 carbon atoms, alkoxy having 1 to 4 carbon atoms, " and substitute -- consisting of alkyl having 1 to 4 carbon atoms, alkoxy having 1 to 4 carbon atoms, alkylthio having 1 to 4 carbon atoms, halogenoalkyl having 1 to 4 carbon atoms and --

Signed and Sealed this

Thirteenth Day of August, 1996

*Attest:*

BRUCE LEHMAN

*Attesting Officer*     Commissioner of Patents and Trademarks